(12) United States Patent
Hannemann et al.

(10) Patent No.: US 10,609,494 B2
(45) Date of Patent: Mar. 31, 2020

(54) METHOD FOR OPERATING A HEARING DEVICE AND HEARING DEVICE

(71) Applicant: SIVANTOS PTE. LTD., Singapore (SG)

(72) Inventors: Ronny Hannemann, Buckenhof (DE); Daniel J. Strauss, Saarbruecken (DE); Farah I. Corona-Strauss, Saarbruecken (DE)

(73) Assignee: Sivantos Pte. Ltd., Singapore (SG)

( * ) Notice: Subject to any disclaimer, the term of this patent is extended or adjusted under 35 U.S.C. 154(b) by 39 days.

(21) Appl. No.: 16/102,988

(22) Filed: Aug. 14, 2018

(65) Prior Publication Data

US 2019/0052978 A1 Feb. 14, 2019

(30) Foreign Application Priority Data

Aug. 14, 2017 (DE) .................. 10 2017 214 164

(51) Int. Cl.
  *H04R 25/00* (2006.01)
  *A61B 5/0492* (2006.01)
  *A61B 5/0488* (2006.01)

(52) U.S. Cl.
  CPC ......... *H04R 25/505* (2013.01); *A61B 5/0492* (2013.01); *A61B 5/04888* (2013.01);
  (Continued)

(58) Field of Classification Search
  CPC combination set(s) only.
  See application file for complete search history.

(56) References Cited

U.S. PATENT DOCUMENTS

| 6,330,339 B1 | 12/2001 | Ishige et al. |
| 9,025,800 B2 | 5/2015 | Kidmose et al. |

(Continued)

FOREIGN PATENT DOCUMENTS

| JP | H09182193 A | 7/1997 |
| JP | 2014112856 A | 6/2014 |

OTHER PUBLICATIONS

Steven A. Hackley, et al.; "Combined Use of Microreflexes and Event-Related Brain Potentials as Measures of Auditory Selective Attention"; Psychophysiology; Nov. 1987, pp. 632-646; vol. 24 No. 6; USA.

(Continued)

*Primary Examiner* — Duc Nguyen
*Assistant Examiner* — Assad Mohammed
(74) *Attorney, Agent, or Firm* — Laurence A. Greenberg; Werner H. Stemer; Ralph E. Locher (57) ABSTRACT

A method operates a hearing device for a user. In the method, electromyography is performed, in which a muscle activity of an auricular muscle of the user is measured by an electrode array. The muscle activity is continuously measured to detect a complex activity profile of the auricular muscle, in which the user's intention is coded. The electrode array generates a sensor signal that is classified by means of a classifier, and in this classification process, the muscle activity is decoded and the underlying intention is determined by examining whether the sensor signal has a previously known feature vector. The previously known feature vector is assigned to an operating mode of the hearing device, which is set when the sensor signal has the previously known feature vector.

25 Claims, 3 Drawing Sheets

(52) U.S. Cl.
CPC ......... *H04R 25/407* (2013.01); *H04R 25/552* (2013.01); *H04R 25/554* (2013.01); *H04R 25/70* (2013.01); *A61B 2562/0209* (2013.01); *A61B 2562/04* (2013.01); *H04R 25/305* (2013.01); *H04R 25/405* (2013.01); *H04R 25/507* (2013.01); *H04R 2225/41* (2013.01); *H04R 2225/43* (2013.01); *H04R 2460/01* (2013.01)

(56) References Cited

U.S. PATENT DOCUMENTS

| | | |
|---|---|---|
| 2007/0112277 A1 | 5/2007 | Fischer et al. |
| 2010/0160714 A1* | 6/2010 | Chua .................. H04R 25/558 600/25 |
| 2012/0116537 A1* | 5/2012 | Liebetanz ................ A61F 2/72 623/25 |
| 2012/0245655 A1 | 9/2012 | Spitzer et al. |
| 2013/0123656 A1* | 5/2013 | Heck ..................... A63F 13/212 600/546 |
| 2015/0161998 A1* | 6/2015 | Park ....................... G10L 15/24 704/231 |
| 2016/0119726 A1 | 4/2016 | Pontoppidan et al. |
| 2016/0157030 A1 | 6/2016 | Odame et al. |
| 2016/0284363 A1* | 9/2016 | Von Borstel ........... G10L 25/78 |

OTHER PUBLICATIONS

Steven A. Hackley; "Evidence for a Vestigial Pinna-Orienting System in Humans"; Psychophysiology; 2015; pp. 1263-1270; vol. 52 (10); USA.

Daniel J. Strauss, et al.; "Hybrid Wavelet-Support Vector Classification of Waveforms"; Journal of Computational and Applied Mathematics; Nov. 2002; pp. 375-400; vol. 148 Issue 2; published by Elsevier.

F. Yger, et al.; "Wavelet Kernel Learning"; Pattern Recognition; Oct. 2011; pp. 2614-2629; vol. 44 (10); published by Elsevier.

* cited by examiner

METHOD FOR OPERATING A HEARING DEVICE AND HEARING DEVICE

CROSS-REFERENCE TO RELATED APPLICATION

This application claims the priority, under 35 U.S.C. § 119, of German application DE 10 2017 214 164.6, filed Aug. 14, 2017; the prior application is herewith incorporated by reference in its entirety.

BACKGROUND OF THE INVENTION

Field of the Invention

The invention relates to a method for operating a hearing device and to a corresponding hearing device.

A hearing device generally serves to reproduce a sound signal in the direction of a user's ear. The hearing device is worn for this purpose in or on the ear and has a receiver via which a sound is output. A hearing device is especially used to care for a hearing-impaired user. Such a hearing device usually has a number of microphones for receiving sound signals from the environment, and a signal processing unit that appropriately modifies the received sound signals, in particular amplifies them, and then forwards them to the receiver for output.

The benefit of such a hearing device to the user depends essentially on the ability of the hearing device to output the sound signals in such a way that these signals correspond as optimally as possible to the user's needs in a specific situation. First, therefore, the hearing device is adapted to the user's individual hearing profile in the course of a fitting session. This is done by setting a number of operating parameters of the hearing device, which parameters then define the hearing device's behavior during normal operation, i.e. when used in everyday life. In addition, in normal operation, the changing situation and in particular changing environmental conditions are ideally taken into account: for example, whether the user is in a quiet or noisy environment, whether many or few sound sources are present, or the nature of the sound source. To this end, various operating modes are provided, having different settings for the operating parameters. A respective operating mode is then set manually by the user or automatically by the hearing device itself.

For automatic setting, additional sensors are used or the microphone signals generated by the microphones are analyzed. This provides additional information regarding the environmental conditions prevailing at a given point in time. This information is then integrated into an adaptation strategy for the operating parameters of the hearing device during normal operation. For example, certain structures in the microphone signals may be recognized by means of a classifier and thus certain predefined situations may be recognized, e.g. "language," "music" or "background noise". By way of reaction to recognizing a particular environment, an appropriate operating mode is then set, having appropriate operating parameters. Additional sensors may also be used for this purpose, and e.g. acceleration sensors are also possible, by means of which movement of the head is detected, based on which it is concluded that the user wants to hear in a different direction.

The above solutions for improving the settings of the hearing device in operation are only examples out of a great variety of possibilities. Common to these approaches, however, is that they are dependent on sensors, which inherently detect external influences and are therefore susceptible to errors, and are especially prone to misinterpretations regarding user intent. If, for example, a sudden new sound is measured in one direction, this fact does not necessarily mean that the user wants to change the hearing direction; it could be an insignificant distraction. The actual user's intention remains unknown in principle. Another idea is therefore to measure brain waves and generate an electroencephalogram (EEG). The brain waves measured by EEG are the sum of different nerve signals. Because the user's own brain waves are generated in response to the current situation, some degree of intention may already be presumed, so that the brain waves as signals are highly likely to be relevant to the current situation. To measure the brain waves, an electrode array is attached, with a plurality of electrodes distributed over the user's scalp. Certain reactions of the user then generate a specific pattern of brain waves, so that upon recognizing these patterns the hearing device, or more precisely the operating parameters, may be adjusted in a precise way. However, an EEG measurement is very expensive in terms of apparatus. An EEG is therefore on the whole not suitable for everyday use.

In U.S. patent publication No. 2012/0245655 A1, in contrast to pure measurement of brain waves, a measurement of a muscle reflex is described, namely a reflex of the posterior auricular muscle (or post-auricular muscle), which is why the reflex is referred to as PAMR, short for post-auricular muscle reflex. This reflex is triggered by an acoustic stimulus, notably a loud sudden noise, such as a bang. By measuring just that reflex, it is then possible to recognize a reflexive reaction of a person to a corresponding acoustic stimulus. The reflex of the posterior auricular muscle is measured by means of an electrode array having a multiplicity of electrodes. When a signal rises or a threshold value is reached, the reflex is detected. Based on this recognition, the operating characteristics of the hearing device may then be adjusted.

SUMMARY OF THE INVENTION

Against this background, it is an objective of the invention to provide an improved method for operating a hearing device, and a corresponding hearing device. A number of operating parameters of the hearing device should be as reliable as possible, with respect to the needs of a user in a specific situation. The method and the hearing device should additionally be as suitable for everyday use as possible.

The objective is achieved, according to the invention, by a method having the features according to the main method and by a hearing device having the features according to the main device claim. Advantageous embodiments, developments and variants are the subject matter of the dependent claims. The statements made in relation to the method also apply analogously to the hearing device, and vice versa.

The method is used for operating a hearing device. The hearing device is configured to be used by a user. In the method, electromyography is performed in which muscle activity of an auricular muscle of the user is measured by means of an electrode array. The muscle activity is in particular the result of an orientation activity of the auricular muscle, to align the appropriate ear of the user; this orientation activity is however greatly evolutionarily underdeveloped in humans, and therefore only rudimentary. The muscle activity is measured continuously to detect a complex activity profile of the auricular muscle in which a user's intention is coded; that is, the user's intention is coded in the muscle activity. The intention is also especially referred to as a hearing intention. The electrode array generates a sensor signal which is classified by means of a classifier. In the classification process, the muscle activity is decoded and the underlying intention is determined by examining whether the sensor signal has a previously known feature vector that belongs to a previously known class. The previously known feature vector, i.e. the previously known class, is assigned to an operating mode of the hearing device which is set if the sensor signal has the previously known feature vector, i.e. if the intention is recognized. Thus, the user's intention is determined based on the muscle activity of the auricular muscles and the hearing device is set based on this intention, i.e. a certain operating mode is set that is associated with the intention, in order to ensure optimal operation in that situation, which is the reason for the intention.

The operation of the hearing device is defined at a given time by particular values for a number of operating parameters. These operating parameters and their values make up an operating mode of the hearing device. An operating parameter is, for example, an amplification factor by which incoming sound signals are amplified before being output to the user. A respective operating mode serves to optimally adapt the behavior of the hearing device, in a specific situation assigned to the operating mode, to the needs of the user in that specific situation. "Setting an operating mode" refers to setting one or more operating parameters in a predetermined manner, e.g. to certain values. In principle, a plurality of operating modes may also be set at the same time, the values of the operating parameters then being the result, for example, of averaging the values of different operating modes.

In the present method, electromyography (EMG) is performed, in which by means of an electrode array, an auricular muscle activity of the user is measured. This muscle activity is the result of a nerve signal that is sent from the brain to the auricular muscle. Accordingly, a bioelectrical signal, i.e. an electrical potential of the auricular muscle, is measured by means of the electrode array. The bioelectric signal comes from the auricular muscle; thus, in contrast to an EEG, what is measured is not the nerve signal of the brain, but a signal on the auricular muscle. It is a particularly significant advantage of EMG measurement that the signal to be measured is significantly stronger and more isolated than in an EEG measurement. An EEG measurement measures the nerve signal sent by the brain, but this nerve signal is amplified at the auricular muscle via additional motor nerve units, so that a stronger signal is available for the EMG measurement. The auricular muscle, which is located further toward the exterior of the head than the brain is, is also not affected by the numerous other signals and reactions of other nerves and muscles; in contrast, an EEG necessarily measures a superposition of a variety of nerve signals. In other words, the EMG signal is already naturally filtered and amplified. In the case of an EMG, the signal quality is significantly better compared to an EEG, and more useful signal is available for analysis. This eliminates the need for a corresponding expenditure on equipment for signal processing, making the hearing device significantly more compact and suitable for everyday use. Furthermore, the sensor signal of the EMG measurement has higher-frequency components than an EEG measurement, so that an EMG measurement may be carried out comparatively more quickly, yielding a shorter measurement time.

The electrode array is used to create the sensor signal. For this purpose, the electrode array has a number of individual electrodes or poles, which are arranged at different locations on the user's head. An individual electrode is also an individual electrical contact. In order to measure the muscle activity, the potential difference between two different electrodes is measured. The potential difference then yields the sensor signal and in particular corresponds thereto. The electrode array is therefore designed to be multipolar, so as to measure the sensor signal as a potential difference between two individual contacts at different locations on the user's head.

In the context of this application, "auricular muscle" refers to one of the muscles that make up the human auricular musculature. The auricular musculature consists of the auricularis anterior, auricularis posterior, auricularis superior, helicis major, helicis minor, transversus auriculae, obliquus auriculae, tragicus and antitragicus muscles. The above list is exhaustive. Preferably, in the method, the auricular muscle is one of the three extrinsic auricular muscles, i.e. the auricularis anterior, posterior, and superior, most preferably the auricularis posterior because it lies in the support region of a hearing device worn behind the ear.

The auricular muscles no longer fulfill a relevant function in humans, at least in modern times, but they are nevertheless activated by the brain in some situations and above all in response to acoustic stimuli. A truly volitional excitation of the auricular muscles is not possible for most people, however, in the vast majority of people a stimulation by the brain is volitionally controlled, inasmuch as the auricular musculature is stimulated in intentional, i.e. intended actions of a person. The muscle activity detected by means of the electrode array is then an orientation activity, i.e. an activity aimed at aligning the ear, but this effort is ultimately fruitless because such an orientation of the ears is actually impossible in humans. However, the ability to intentionally align the ears with the auricular musculature is present in some animals. The phenomenon is described in detail in Hackley et al. "Combined Use of Microreflexes and Event-Related Brain Potentials as Measures of Auditory Selective Attention", November 1987, Psychophysiology Vol. 24, No. 6 632ff and Hackley "Evidence for a Vestigial Pinna-Orienting System in Humans", 2015, Psychophysiology, Vol. 52, 1263ff. The present invention exploits the knowledge that in humans, a muscle activity takes place together with a corresponding intention.

The measurement of muscle activity, i.e. in general the activity of the user's auricular muscles or the behavior of one or more of the muscles of the auricular musculature, represents a core concept of the invention. This approach is based on the recognition that the muscle activity of the auricular muscles is caused by the user's brain, so that in the presence of a certain situation with certain stimuli, it has already been decided by the brain, and thus by the user, that a potentially relevant stimulus is present. For sensors that measure only external effects such as volume, acceleration or the like, the user himself or herself cannot make a preliminary decision by means of the brain. In other words, the goal is to correlate an intention, more precisely a hearing user's intention, with the activity of the auricular muscles. The auricular muscles become active especially in the case of a conscious hearing intention, in which the user strives to listen to a specific sound signal, for example in a certain direction.

A user's intention is therefore coded in the muscle activity, because the muscle activity is not merely reflexive, but also results from a voluntary effort, as Hackley (2015, supra) describes. Muscle activity is therefore also an expression of the user's desire to hear in a certain direction or in a certain way or to hear a certain stimulus. As a result of this hearing intention, the brain causes an excitation of the auricular musculature. The brain and the auricular muscles thus act like a classifier, i.e. the current situation is classified by the brain in such a way that in response to this situation, a muscle activity should occur to orient the auricular muscles. In the present method, therefore, the user's deliberate hearing intention is decoded from the muscle activity of the auricular muscles and is then used to adjust the hearing device.

Adjustment of the hearing device is thus not, or at least not solely, caused directly by the user's environment, and may be independent of the user's intention. Rather, what is exploited is that the muscle activity also indicates a specific relevance of the current situation for hearing, so that an adjustment is carried out with knowledge of the user's intention, and thus, advantageously, exactly when the user wants it. The user's intention is accordingly taken into account on the basis of the activity of the auricular muscles, and then the hearing device is adjusted, and in consequence the adjustment is significantly more needs-based and less error-prone. Incorrect settings are advantageously avoided.

A key aspect of measuring muscle activity is not merely measuring a reflex. In the present case, it has been recognized that a reflexive response to an abrupt, bang-like acoustic stimulus is only one element of a clearly more complex muscle activity. The auricular musculature not only responds reflexively and rapidly to specific stimuli and situations, but the response also continues over a longer period of time, e.g. several seconds, depending on the situation and is not merely reflexive, but also expresses user intention. Typically, a reflex of the auricular muscle results from the perception of a sudden acoustic stimulus such as a bang, and occurs within a period of up to 25 ms after the sound signal reaches the ear. As part of the reflex, a particularly strong change may be measured in the potential of the auricular muscle. This is exploited in the aforementioned U.S. patent publication No. 2012/0245655 A1.

But in the method of the present application, what is measured is not a mere reflexive muscle reaction, but also muscle activity, i.e. the response behavior of the auricular muscle beyond a short-term reflex. Apart from a simple reflex, the auricular musculature also exhibits a significantly more complex activity profile, which is measured in the present method by continuously measuring muscle activity. For example, it has been found in the present case that the muscle activity does not have only isolated individual signal bursts, as in the reflexive response, but whole sequences of related signal bursts. In contrast to a reflex measurement, therefore, monitoring of the total muscle activity of the auricular muscle is not triggered at a certain threshold value; rather, measurement is performed over a longer period of time, to capture the entire complex activity profile of the auricular muscle. Accordingly, "continuous" means in particular that the muscle activity is not triggered by the sensor signal itself, but takes place rather over a specific measurement period, which is, in particular, independent of the sensor signal. The long-term measurement does not merely average over a plurality of repeatedly occurring signals, but instead serves to detect complex activity profiles that would not be included in a measurement that was merely triggered or short-term. As a result, in addition to possible reflexes, possibly ongoing muscle activity is also recorded, measured and evaluated. Advantageously, a sound source to which the user does not want to listen and with respect to which the user does not express a hearing intention is disregarded by the hearing device and does not lead to a different setting, although the hearing device may have already identified the presence of this sound source in other ways, for example by analyzing a microphone signal.

By measuring the behavior of an auricular muscle over a relatively long period of time, a complex signal profile of the sensor signal is produced, which is then searched for patterns in order to classify the sensor signal and decode the user's intention. In particular, the patterns searched for are much more complicated, and thus situation-specific, than in the case of a simple reflex. However, a single reflex as described above is not necessarily meaningless; rather, a plurality of reflexes are detected together by measurement over a longer period of time, and these are then evaluated for example as a reflex group, which may describe a specific user's intention. Long-term measurement is advantageously not limited to the measurement of reflexes; rather, the long-term behavior of the auricular muscle is measured. Preferably, measurement of reflexes may be completely dispensed with, because usually no user intention is coded therein—since it is merely a reflex.

The sensor signal is in particular a voltage that changes as a function of the muscle activity, or more precisely as a function of the potential of the muscle and is, for example, proportional thereto. The sensor signal is classified by means of a classifier, i.e. it is subjected to a classification and compared with previously known feature vectors in order to assign the sensor signal to a class. Beforehand, however, the sensor signal is expediently prefiltered in a prefilter, in particular with noise artifacts removed. A feature vector generally has a number of features, typically a plurality. These features are, for example, specific amplitudes, threshold values, specific traces, signal sequences or the mere presence of specific signals or signal components in the overall sensor signal. The sensor signal is therefore examined with regard to such features. If the features of a feature vector are sufficiently clear, i.e. within a tolerance range, the feature vector is detected in the sensor signal. Each previously known feature vector then corresponds to a particular muscle activity. This is based on the consideration that every user's intention generates a specific signature in the muscle activity, which is characterized by a number of features and accordingly by a feature vector, and may be classified by that means. Each previously known feature vector therefore corresponds to a user's intention, so that by a classification of the sensor signal and a determination of the feature vectors contained therein, the intentions of the user are decoded and used as control commands for the hearing device. As a result of the continuous measurement of, in particular, sustained muscle activity, complex and time-stable feature vectors are detected so that a particularly differentiated recognition of the user's intention is possible, and indeed takes place. Evaluation of the sensor signal is thus not particularly limited to small time periods of less than 100 ms, but may also occur on a larger time scale, so that complex and ongoing activity is reliably detected.

As already indicated, in the space of the feature vectors, a number of classes are formed, to which the feature vectors are assigned; in other words, the previously known feature vectors are each assigned to a class. The feature vector that is determined in the sensor signal, that is to say the feature vector of the sensor signal, is then assigned to one of the classes depending on the configuration, i.e. depending on the specific features. A class thus is as a set of similar feature vectors. In this case, a respective class covers a subspace of the entire space of the feature vectors, i.e. it is a subset which contains all those feature vectors that are assigned to the same operating mode, being sufficiently similar. However, below, the term "previously known feature vector" will sometimes be used instead of the term "class."

The degree of organization or the energy of the sensor signal, or both, is preferably used as a feature. A preferred measure of the degree of organization is the entropy of the sensor signal, the entropy being defined as the change of the sensor signal over time, in particular within the measurement period. In this case, for example, the change in the amplitude is examined. The energy is defined as the integral over the sensor signal over time, especially within the measurement period. In one variant, to determine the energy, the sensor signal is weighted with an exponent, i.e. a higher-order norm is used, such as a quadratic norm. A low norm leads to reduced in-class variance: the multiple feature vectors of a single class vary less and are therefore more similar. In contrast, a high norm leads to reduced inter-class variance, and the similarity of the feature vectors assigned to a class is reduced; however, differences of the feature vectors to each other are emphasized more, so that more finely-resolved classes may be formed. In the present case, the lowest possible norm, in particular an L1 norm, is preferred.

More preferably, a plurality of the aforementioned features are formed by performing the corresponding examination in different frequency bands. The sensor signal within a particular measurement period is thus considered in the frequency domain and divided into a plurality of frequency bands, which are each separately examined for their entropy, energy or both. In the latter case, there are twice as many features as frequency bands. The previously known feature vectors are then characterized by particular values, ranges of values, threshold values, limit values, change patterns, traces, or the like for one or more of the features.

The response behavior of the auricular muscle is monitored in particular continuously and thereby a correspondingly continuous sensor signal is generated, the course of which allows a much more extensive analysis than in the case of either short-term measurement or averaging over several short windows. "Longer time" should preferably be understood to mean a period of time, i.e. a measurement period, which is longer than a single reflex of the auricular muscle and which is in particular longer than 25 ms, preferably longer than 100 ms and particularly preferably longer than 1 s. The previously known feature vector is searched for in the sensor signal over the entire measurement period. This ensures that those feature vectors are also recognized that represent longer and more lasting muscle activity. This is based on the consideration that a feature vector does not necessarily contain only a single feature or those features that are present simultaneously, but that in the context of the complex activity profile of the auricular muscle, time-staggered features are also caused by a single intention and may be assigned thereto, or conversely, that the intention is defined by temporally spaced features. By examining the entire longer measurement period, feature vectors are thus also recognized that describe a particular dynamic of the muscle activity and not merely brief reflexes. An upper limit is generally not given, but expediently the measurement period is not longer than 10 s, because reactions that are farther apart than that usually do not belong together and therefore usually have no added value with regard to the evaluation. On the other hand, too long a measurement period would slow the response speed of the hearing device by too much, because the hearing device would only recognize the user's intention after a considerable time delay, and would be correspondingly slow to respond. Particularly expedient is a so-called rolling period that moves continuously over time.

The monitoring of muscle activity of the auricular musculature offers a multiplicity of potential applications. The above-described classification, in particular in combination with the concepts for learning new feature vectors described below, enables a reaction to any activity of the auricular muscle.

Because the auricular muscles basically aim at any activation of an orientation activity of the ears, monitoring the muscle activity is particularly suitable for setting a directional characteristic (or "directivity") of the hearing device, for adaptation to directional hearing. During directional hearing, the hearing device outputs the received sound signals of the environment to the user in such a way that sound signals from a specific direction, namely a hearing direction, are amplified relative to the remaining sound signals. As a result, sound signals from the hearing direction are preferentially reproduced. In an advantageous embodiment, the hearing device is configured for directional hearing and a directivity of the hearing device is adjusted based on the muscle activity, and by this means a sound source is emphasized in a particular direction. The directivity is in particular a directional beam defined by a width and an angle. Sound sources within the directional beam are amplified by the hearing device more than sound sources outside the directional beam. The angle indicates the direction in which the directional beam is oriented with respect to the user. The width indicates the angular range that the directional beam covers. The angle and the width, in this case, are each respectively operating parameters, which together form the operating mode "directional hearing in a specific hearing direction."

When setting the directivity, the knowledge is exploited that the muscle activity, in evolutionary biology terms, is intended to effect an alignment of the ears, inasmuch as an intention to hear in a particular direction is coded in the muscle activity of the auricular muscles. The ears are not actually aligned, as already stated, but the control signals are still sent to the auricular muscles and have a corresponding signature, which results in a corresponding activity profile and is usually user-specific. By recognizing this signature, i.e. the associated feature vector, the intention of directional hearing is recognized. In a variant of this, it is not only recognized that directional hearing is desired, but in addition, the desired hearing direction is recognized. The same applies to the width of the directional beam.

The signature during directional hearing consists in particular of a sequence of signal peaks, i.e. the sensor signal has an increased amplitude at specific, defined, and, in particular, constant intervals. In directional hearing, a sequence of signal peaks is therefore preferably sought in the sensor signal. In directional hearing in particular, the distances are such that the signal peaks in the frequency space yield a high-frequency signal component, in particular in the range between 500 Hz and 1000 Hz.

In a particularly preferred embodiment, the hearing device is a binaural hearing device and has two individual devices, to be worn on different sides of the user's head. The current situation is then recognized by measuring a muscle activity of a local auricular muscle on each side, by means of a respective electrode array. In this embodiment, therefore, two sensor signals are advantageously available and thus more information overall, i.e. more features, are available for classifying the user's intention and for improving the selection of a suitable operating mode. In principle, however, a monoaural hearing device, having only a single individual device for only one ear of the user, is also suitable.

Preferably, the muscle activities on both sides of the head are first evaluated separately by classifying the sensor signals (S) independently of one another, and then the hearing device is set accordingly if the results agree. In particular, the hearing device is set only if the results agree. Thus, a comparative decision making process takes place, in which the result depends on comparing two independently evaluated sensor signals. The two classifiers each independently provide a classification result and the two classification results are compared with each other. If the two classification results match, the hearing device is adjusted accordingly. In other words, the operating mode is initially determined redundantly, by the two sensor signals being classified separately, so that two operating modes are determined. If the two operating modes are the same, i.e. the same intention was recognized for both sides, a corresponding operating mode is set. Otherwise, no adjustment of the hearing device is particularly made in response to the muscle activity. This prevents miscalculations. In one variant, a mixed operation is set, which results from a sort of compromise, a mixture of the two operating modes that were determined.

Additionally or alternatively, the muscle activities on both sides are first evaluated separately by classifying the sensor signals independently, and if the results are different, the individual devices are synchronized by adjusting one of the individual devices against its own result and with reference to the result of the other individual device. In the case of different results, and more precise classification results, different optimal operating modes are also determined. Instead of making an adjustment only if the result is the same as described above, it is attempted to reach an agreement between the two results of the individual devices, in order to set an operating mode that is as optimal as possible, even if the results of the evaluation of the sensor signals are divergent. For example, in the case of differing results, an additional sensor is additionally evaluated in order to decide which of the two results to use and which operating mode to set. Alternatively or additionally, one of the two individual devices is preset, e.g. trained in a training procedure, and in the case of a differing result, it then trains the other individual device by setting the operating mode determined by the preset individual device.

The binaural hearing device described above is particularly suitable for setting directivity as described above in the context of directional hearing, i.e. directed hearing.

In a suitable embodiment for directional hearing, a desired hearing direction, i.e. an intention is preferably determined, in particular qualitatively, by examining which of the two sensor signals has a higher degree of organization or a higher energy. The sound source is then located on this side. The directivity is then adjusted toward the hearing direction. This is based on the consideration that with a lateral sound source, i.e. a sound source that is not frontal and not centrally positioned, only the ear on the corresponding side would need to be oriented, and accordingly a particular effort of the auricular musculature on this side may be measured, while the other side largely remains idle, so that the sensor signal has a lower degree of organization. This qualitative determination of the hearing intention is advantageously less user-specific and therefore generalizable. By "higher degree of organization" is generally meant in particular that more features, or even any features, are found in the corresponding sensor signal, and in particular especially that on one side the entropy in one or more or all frequency bands is greater than on the other side. By "higher energy" is meant in this case that on one side the energy in one, several or all frequency bands is higher, the energy being particularly determined as already described above.

Alternatively or in addition to the above-described qualitative examination, the intended hearing direction is determined quantitatively, in particular in determining the direction or the width of the directional beam, or both. Again, the muscle activity is evaluated accordingly. The sensor signals are evaluated either redundantly on both sides, as described above, or together or in combination and e.g. in succession. When evaluated together, a feature vector is composed of features of both sides; in other words, the features on both sides are used in combination to determine a feature vector that spans both sides in the sensor signal and to compare this vector to corresponding previously known feature vectors. In this way, the feature count is advantageously increased and the determination of the suitable operating mode becomes even more specific.

However, the orientation activity of the auricular muscles does not merely encode a hearing intention; rather, the orientation of the auricular muscles may also be understood as part of the user's facial expression. In particular, a change in facial expression or a movement of individual parts of the face has an effect on the auricular muscles. Of particular interest in the present case is muscle activity of the auricular muscle during speech and when forming a facial expression.

In a preferred embodiment, muscle activity in speech is used for own-voice detection. On the basis of the muscle activity, an own-voice situation is recognized, in which the user is speaking. The operating mode that is set in that case is an own-voice reduction, in which an own-voice component in an output signal of the hearing device is reduced, and in particular is filtered out. In a binaural hearing device, this is preferably done by means of a binaural computation, i.e. by a suitable combination of microphone signals from both sides of the user's head.

In an expedient development, not only is an own-voice situation recognized as such, but what exactly is being said is also recognized, so that speech recognition takes place. The natural voice component is then specifically and effectively reduced or even completely eliminated. In a first variant, speech recognition by use of an additional sensor, and the own-voice recognition based on the muscle activity, are used as additional information to support speech recognition. This is based on the consideration that an additional sensor, such as a microphone, may not distinguish optimally between the voice of its own user and those of others, depending on the circumstances. The own-voice recognition as additional information then supports speech recognition in that a clearer distinction is made between the user's own voice and voices of others. Speech recognition is carried out, for example, by means of a classifier, which examines the microphone signals, so that the additional consideration of the muscle activity provides further features and in this way supports the classifier. In a second variant, which may also be used in addition, speech recognition takes place solely on the basis of muscle activity and not to support an additional sensor; the sensor signal is thus evaluated in such a way that a determination is made that the user is speaking, and in particular exactly what the user has said is determined, directly from the muscle activity.

Alternatively or additionally, through speech recognition, speech recognition is realized in which the hearing device is adjusted via voice commands, without having to evaluate microphone signals that may contain interference signals or foreign voices.

In a preferred embodiment, a facial expression of the user is recognized based on muscle activity, and this expression is used as a control command for setting a particular operating mode that is assigned to the control command. The muscle activity thus generally serves as a control command for the hearing device. The user forms a facial expression, which entails a certain muscle activity, which is then recognized. As a result, emotions and thus intentions in a broader sense may be recognized, and a suitable operating mode may be selected on that basis. In one variant, an emotion of the user is then determined on the basis of the muscle activity and the intention is derived from this information. The fact that emotion is expressed in a specific facial expression, which also affects the auricular muscles, is exploited.

Particularly advantageous is an embodiment in which, if the sensor signal has a feature vector which is merely similar to the previously known feature vector, faulty positioning of the hearing device is detected based on the muscle activity. In this way, it may be reliably detected whether the hearing device is being worn correctly or whether there is a deviation from a predetermined wearing position. In this context, "similar" is understood in particular to mean that the feature vector that has been found in the sensor signal has a certain degree of agreement with the previously known feature vector, but that the deviation therefrom is greater than a tolerance within which the feature vector in the sensor signal would be deemed consistent with the previously known feature vector. This is the case, for example, if the two feature vectors only agree in some features or if some or all of the features have slightly divergent values.

In a suitable embodiment, the two feature vectors are compared with respect to their amplitude to determine whether there has been a faulty positioning. To this end, for example, the energy in each of the frequency bands is used as a feature. This is based on the consideration that, if the electrode array is not positioned correctly, it is usually further away from the auricular muscle and as a result the sensor signal as a whole is weaker, so that the features are likewise correspondingly less distinct. On the other hand, the electrode array may also be located opposite the usual wearing position, in such a way that an overall stronger sensor signal is then measured.

Alternatively or additionally, the regularity of the two feature vectors is determined and compared. The regularity indicates, in particular, the relationship of individual frequency components to one another, i.e. the ratio two frequency components have to one another. Here again, for example, the energy of the individual frequency bands is used to first determine the regularity of a feature vector by comparing the energies of two frequency bands and then comparing the regularities of the previously known feature vector and the feature vector in the sensor signal. In this respect, an actual regularity of the feature vector in the sensor signal is compared with a desired regularity of the previously known feature vector, in order to detect faulty positioning.

In the context of detecting faulty positioning, the previously known feature vector is, in particular, an expected feature vector, i.e. in the examination of the sensor signal, the previously known feature vector is expected, but a feature vector is found that is similar but deviates therefrom. In an expedient development, the previously known feature vector is selected as the expected feature vector from among a plurality of previously known feature vectors by additionally determining which operating mode is set or which situation is currently present, and by selecting the previously known feature vector that is assigned to that operating mode or situation. When detecting faulty positioning, therefore, knowledge of the current situation or current operating mode is utilized to determine which feature vector is actually expected in the sensor signal. The operating mode or the current situation is expediently determined by an additional sensor, for example a microphone the signal of which is subjected to an audio analysis.

In an expedient development, faulty positioning is recognized and corrected by supplying a measure of the faulty positioning as an actual value in a control loop. For example, a current feature vector, or a specific value for a number of features in the sensor signal, is used as a measure in the sensor signal. The previously known feature vector, which corresponds to the optimal positioning, is then in particular a setpoint for the control loop. Expediently, a warning is issued when there is a faulty positioning, inducing the user to adjust the positioning.

Overall, therefore, adjustments may advantageously be realized by recognizing the user's intention by measuring the muscle activity. The setting of a directional characteristic has already been mentioned. In the context of the embodiments already described, or alternatively or additionally, as the operating mode, a specific amplification scheme, a specific compression scheme, i.e. frequency compression scheme, a noise suppression or other algorithm, or a combination thereof, may be set. Such settings are particularly advantageous in combination with the own-voice recognition described above, because a change in the operating mode usually is appropriate in a natural voice situation. When changing from or to an own-voice situation, appropriate adjustments are expediently made, which suppress, for example, the natural voice component as described above. When recognizing a facial expression as well, it is reasonable to set or adapt the operating mode to respond to the situation that most likely has changed.

The adjustment of the hearing device based on the muscle activity is automatic. Expediently, however, the selected setting may be prevented, in particular by the user overwriting the result of the automatic recognition by a manual input.

Advantageously, in addition to decoding the user's intention based on the previously known feature vectors V, there is also a receiving, i.e. recording, of new feature vectors N in order to recognize new and previously unknown intentions in the future. The method then also contains a learning process in which the hearing device learns new feature vectors and then stores them as previously known feature vectors. This is based on the knowledge that the muscle activity of the auricular muscles is at least partially individual among users, so that the same intention may be characterized by different features in different users. Conversely, the same feature vector may in principle also be generated by different intentions in different users. Expediently, therefore, individual adaptation takes place by adopting new feature vectors. In a suitable embodiment, a number of new feature vectors are then received, i.e. recorded, and stored in memory as a corresponding number of previously known feature vectors, in order to be able subsequently to examine the sensor signal for these feature vectors that are previously known and thus have been learned.

In a particularly preferred embodiment, to learn new feature vectors, the sensor signal is additionally subjected to feature extraction by means of a feature extractor, in which a new and in particular an individual, i.e. user-specific, feature vector is generated, which is then stored as an additional previously known feature vector. A new feature vector is then extracted from the sensor signal and stored in memory in order to use it in the future as a previously known feature vector. The new feature vector is, in this case, a learned feature vector. Overall, the hearing device defines and learns a new class, which is henceforth available for classification.

A training procedure is expediently carried out for adopting a new feature vector. In the course of the training procedure, certain intentions of the user are deliberately induced in a training situation, for example by certain stimuli that give rise to a muscle activity the characteristics of which are stored as a new feature vector. The associated intention is specifically caused by the training situation and is thus sufficiently known that a reliable assignment is ensured. In one variant, the training procedure is carried out at an audiology practice. Alternatively or additionally, the training procedure is performed by the user himself or herself, for example, supported by training software or a training mode of the hearing device. The training procedure is suitably carried out in various situations and environments in order to additionally reliably recognize different intentions in different situations and environments, i.e. situation-specifically.

The previously known feature vectors, i.e. classes, may in principle be predefined in various ways. Feature vectors may be predefined in the production of the hearing device as, essentially, factory-installed feature vectors. However, these factory-installed feature vectors do not take into account the individual response behavior of the auricular muscles of the respective user, and are therefore limited in particular to such feature vectors as may be generalized independently of the user. On the other hand, additional feature vectors may be added as described above in the course of a training procedure, e.g. an individual fitting session for the user. In this case, the user is specifically presented with certain stimuli and then the user's individual response behavior is measured, in order to derive and store in memory a new and individual feature vector from the resulting sensor signal for the presented stimulus and the associated intention. In the same way, in one variant, already known feature vectors are adapted, i.e. the previously known feature vectors are fine-tuned.

In a suitable embodiment, the previously known feature vector is taken from an external database, which is stored for example on a server. The previously known feature vector is therefore initially not stored in the hearing device, but is requested from the external database by the hearing device or automatically transmitted by the external database. In particular, the external database contains a multiplicity of previously known feature vectors and serves as a central storage location. New feature vectors are expediently stored in the external database and are then advantageously also available to other users. As a result, the learning time, i.e. the expense of extracting new feature vectors, may be drastically reduced. Although the muscle activity is highly individualized, the method still benefits from the feature vectors that were determined in conjunction with another user, by using the feature vectors of another user as seed values when recognizing a new feature vector and then optimizing these seed values user-specifically. Moreover, the storage of the feature vectors in an external database also permits a meta-analysis by which advantageously generalizable feature vectors, i.e. feature vectors which are not user-specific or are user-specific only to a limited extent, may be determined. In this respect, the new feature vectors of a plurality of users in the external database are then combined and generalized to determine generalized feature vectors, which in turn are available to a single user as previously known feature vectors and are used in the operation of the hearing device to classify the sensor signal.

Particularly advantageous is an embodiment in which individual feature vectors are automatically learned through a machine learning process. As a result, learned feature vectors are generated and stored and incorporated in subsequent analyses as (now) previously known feature vectors. The analysis of the muscle activity is particularly suitable for a machine learning process, because the muscle activity is highly individualized and thus may only be generalized to a limited extent. In contrast, for example, the classification of noise environments based on microphone signals may be generalized very readily, because a noise environment is characterized by certain sounds and thus is characterized by a feature vector that is known a priori. In contrast, the response behavior of the auricular muscle, which is generated individually by the brain of the user, seldom produces a feature vector which is the same independently of the user for a particular situation. In the machine learning process, a user-specific set of feature vectors is generated.

The machine learning process is performed by a learning machine. This is preferably a part of a control unit of the hearing device and particularly preferably is integrated into a housing of the hearing device. Alternatively or additionally, the learning machine is arranged externally, for example on a smartphone of the user or on a server.

A particularly suitable machine learning process for feature extraction is described in Strauss and Steidl, "Hybrid wavelet-support vector classification of waveforms", Journal of Computational and Applied Mathematics 148 (2002), p. 375-400. The method described there is preferably also used for classification, i.e. for the recognition of previously known feature vectors in the sensor signal, in particular feature vectors previously learned by feature extraction. Accordingly, the classifier is preferably implemented by a support vector machine (SVM) which, as part of the machine learning process, maximally discriminates against the different feature vectors, i.e. classes that are assigned to different operating modes; by this means, a particularly reliable classification, i.e. recognition of previously known feature vectors, is ensured. At the same time, this advantage also benefits feature extraction, because corresponding newly learned feature vectors may be optimally distinguished automatically.

In a preferred embodiment, the new feature vector is generated in a supervised machine learning process. The learning machine is thus trained in a learning process. A certain situation with a still unknown feature vector is assigned to a certain operating mode. The generally known operating mode for the generally known situation should now be able to be set by detecting the muscle activity, but the particular individual muscle activity is still unknown. In the course of the machine learning process, in a training procedure the specific situation is established as the current situation, and by this means, a corresponding user's intention is created, which is then characterized by a feature vector which is determined and linked to the operating mode. To this end, the feature extractor independently searches for a number of unknown features in the sensor signal. The unknown features are then combined to form the new feature vector and this vector is assigned to the particular operating mode. The new feature vector is then a learned feature vector and is henceforth available as a previously known feature vector.

It is essential to the machine learning process that the features are not initially predetermined, but are determined independently by the feature extractor. For this purpose, the feature extractor examines the sensor signal according to patterns or regularities and in particular according to features which in combination do not correspond to any previously known feature vector. But in a variant, features which are similar to a previously known feature vector are explicitly searched for in order to refine or adapt the representation thereof. The situation which is set for this purpose is expediently the same situation which, via the associated intention, is assigned to the feature vector to be improved.

Particularly advantageous is an embodiment in which a machine learning process, particularly one as described above, is performed during normal operation of the hearing device, i.e. when the device is worn in everyday life and outside of any special training situation. The feature extractor then continuously examines whether new features or new feature vectors, which are not previously known, are included in the sensor signal. At the same time, the current situation or the operating mode that is currently set, or both, are detected and assigned to the feature vector. This is based on the consideration that the respective situation reproducibly generates a specific user intention and requires a specific operating mode. By incorporating the feature vector that is characteristic for this situation or the operating mode or both, the situation will then reliably be recognized again in the future, and the suitable operating mode will be set.

In the context of a hybrid analysis, whether the current situation is a previously known situation to which a previously known operating mode has already been assigned is suitably recognized by means of an additional sensor, and if the current situation corresponds to the previously known situation, the new feature vector is assigned to the previously known operating mode. Thus, in particular, a learning process is realized in which the hearing device automatically generates new associations between the muscle activity and the current situation. The problem of the assignment of the feature vector to a specific situation and to a specific operating mode is solved by an additional sensor so that the process may also be carried out outside of a training situation; in other words, the situation need not be identified from outside. Rather, the additional sensor is used to classify the current situation and identify the optimal operating mode. The required operating mode is then known and may be assigned to the new feature vector. The additional sensor is, for example, a microphone that generates a microphone signal which is subjected to audio analysis in order to classify the current situation and select a suitable operating mode. After the muscle activity and a corresponding feature vector have been learned for this situation, future recognition is correspondingly faster and easier, without needing an expensive audio analysis. Alternatively or additionally, EEG measurement is performed, and in that case the additional sensor is a number of EEG electrodes. An acceleration sensor is also a suitable additional sensor.

In an advantageous embodiment, the previously known feature vector is integrated into a neural network, and by this means, it is examined whether the sensor signal has a previously known feature vector by determining a feature vector of the sensor signal and using that as an input signal for the neural network. An essential advantage of a neural network is in particular that it does not necessarily have to be trained in a supervised learning process, but may also learn and operate unsupervised. A previously known feature vector in this case is not stored in memory, but integrated into the topology of the neural network.

Especially in connection with the previously described embodiment having an additional sensor, therefore, an unsupervised machine learning process may be realized, i.e. the learning machine does not have to be trained, but will learn completely automatically with the aid of the additional sensor. A separate memory for the previously known feature vectors is specifically omitted. Rather, those feature vectors that are integrated into the neural network are now assigned to specific operating modes. In other words: first, by means of an additional sensor, it is recognized whether the current situation is a previously known situation already associated with a previously known operating mode. If the neural network then recognizes the feature vector of the sensor signal, i.e. if a feature vector has been integrated into the neural network and coincides with the feature vector of the sensor signal, this feature vector is assigned to the previously known operating mode. With the aid of the additional sensor, therefore, an assignment of an integrated feature vector to an operating mode is generated in a machine learning process by determining the current situation by means of the additional sensor and then assigning the integrated feature vector to this current situation and thus also assigning it to the operating mode suitable for this situation, which will then be set in the future when the feature vector that has now been learned, i.e. assigned, is again found in the sensor signal. The integrated feature vector thus becomes a previously known feature vector through the learning process.

Analogously to the supervised machine learning process, the unsupervised machine learning process is expediently carried out during normal operation of the hearing device. In the embodiment with a neural network, the neural network then autonomously learns to assign the respective integrated feature vectors to a specific operating mode. This is done for example via an additional sensor as described above, or by feedback from the user.

In a particularly suitable embodiment, the feature extractor and classifier are integrated together in a signal processor and the feature extraction and the classification are treated as a single optimization problem. The classifier and feature extractor then share a single feature recognition, which identifies a number of features in the sensor signal and thus identifies a feature vector. In this way, the overall evaluation of the sensor signal is particularly compact, and in addition, advantageous synergies are exploited that arise from the combined classification and feature extraction, inasmuch as the features only need to be extracted once from the sensor signal and compared with the previously known feature vectors, in order then to generate new feature vectors and also recognize previously known feature vectors. The expense of signal processing is thereby reduced to a minimum. The feature extractor is also advantageously operated in such a way that it extracts those features, and thus feature vectors, that are particularly easy for the classifier to recognize. Because the classifier and the feature extractor use the same feature recognition, they are optimally matched to one another.

The sensor signal is preferably divided into a plurality of frequency bands by a filter bank, with each frequency band forming a number of features. The above-described examination of features based on entropy and energy of individual frequency bands then takes place by means of the filter bank, in such a way that an entropy measurement or energy measurement or both is carried out for each of the frequency bands. A respective measurement of entropy or energy represents a feature, and the features together form a feature vector of the sensor signal. A filter bank is particularly efficient and is particularly suitable for treating feature extraction and classification as a single optimization problem. Because the features for creating new feature vectors are simply taken from the filter bank that is also used for classification, the feature vectors that have been learned once are recognized especially reliably.

The machine learning process is preferably carried out using the hybrid wavelet kernel learning algorithm described in Strauss and Steidl (2002, supra), or also in Yger and Rakotomamonjy "Wavelet kernel learning" Pattern Recognition 44, 2011, p. 2614-2629. The learning algorithm is based on dynamically adapting the underlying wavelets to extract optimal features. This is particularly advantageous in the present case because the features are not yet necessarily known and defined and, moreover, are typically also user-specific. In this respect, in the machine learning process, therefore, advantageously the definition of the features, i.e. specifically the filter bank, is also adapted, e.g. with regard to the limit frequencies of the individual frequency bands. The filter bank is thus a parameterized filter bank. The features defined in this way and the filter bank thus configured are then automatically also optimally suitable for the classification, that is, for examining the sensor signal by means of the signal processing described above.

Preferably, the filter bank is a paraunitary filter bank. A definition of a paraunitary filter bank with two frequency bands is given in Strauss and Steidl (2002, supra) on page 382, in particular in equations (18) and (19). A particularly suitable filter bank with a lattice structure is described in equation (22) therein. The angle mentioned therein serves as a parameter of the filter bank, which in that case is a parameterized and thus advantageously adaptable filter bank.

In a suitable embodiment, the filter bank has ten frequency bands. The frequency bands of the filter bank are preferably respectively octave-wide. This is understood in particular to mean that each frequency band has an upper band limit frequency and a lower band limit frequency, the upper band limit frequency being double the lower band limit frequency. The frequency bands need not be exactly octave wide, however; a deviation of up to 10% is still suitable. Particularly expedient is an embodiment in which the band limit frequencies as already indicated above are adjusted by means of a parameterization, the band limit frequencies being selected in relation to the individual features in such a way that the features are particularly clear.

In a suitable embodiment, the filter bank has a lower limit frequency of 4 Hz and an upper limit frequency of 1 kHz, so that the muscle activity is examined in a frequency range from 4 Hz to 1 kHz.

In a suitable embodiment, in a binaural hearing device, a single filter bank is used to analyze both sensor signals. In particular, the filter bank is then trained by means of the machine learning process in such a way that the filter bank distinguishes the two directions, i.e. in such a way that the filter bank extracts a number of features that are respectively assigned to the left or the right side. Alternatively, however, two separate filter banks are used, one for each individual device.

To generate the sensor signal, the electrode array is formed to be at least bipolar, i.e. to have at least two electrodes, between which a potential difference is measured. In principle, an electrode array with more than two electrodes is also suitable. For EMG measurements in the clinical setting, for example, 128 electrodes are used, which are arranged over the entire head. One of the electrodes is then expediently used as a reference electrode which provides a reference potential against which the other electrodes are each measured in a bipolar arrangement. In other words, the potential difference is measured between each of the electrodes and the reference electrode.

In the present case, the electrode array is formed as compactly as possible. In a suitable embodiment, the electrode array is arranged only in the region of the auricular muscles, i.e. in this context at most 5 cm away from the ear, and more precisely from the auricular musculature, and more preferably at most 2 cm. This ensures that the electrode array is distributed only over a small part of the user's head and thus is particularly suitable for everyday use.

In a preferred embodiment, the electrode array has only at most five electrodes, and more preferably exactly two electrodes. Such a limitation of the number of electrodes also contributes to the compactness of the electrode array and to the suitability of the hearing device and method for everyday use. The reduction in the number of electrodes, especially in comparison to the clinical setting, is based in particular on the observation that a limited number of electrodes is completely sufficient for measuring the muscle activity of the auricular musculature. Especially in connection with a machine learning process, only a small number of electrodes is necessary in order to be able to measure the muscle activity sufficiently accurately and to be able to sufficiently differentiate between different classes.

In a binaural hearing device having two individual devices, two electrode arrays are preferably arranged correspondingly, one for each of the individual devices. The use of only one electrode array per individual device with only a few electrodes as described above is made possible only through the concept of EMG measurement, because a sufficiently filtered and amplified signal is present in this case, as described above. The electrode array is also placed respectively on the auricular muscle and thus in the vicinity of the hearing device. The electrode array is expediently integrated into the hearing device, in particular as part of a housing of the hearing device. As a result, the user's comfort in wearing the device is significantly increased. The impact on visual appearance is minimal. Both contribute to a markedly higher acceptance in everyday applications. Above all, this also makes it possible to measure EMG not only as part of a fitting session with the audiologist using complex equipment, but also unnoticed and invisibly in everyday life, i.e. during normal operation of the hearing device.

Expediently, in addition to the electrodes, the electrode array also has one more electrode that is a reference electrode, in order in particular to monitor the functionality of the remaining electrodes and provide a reference for the signal of the electrodes. In other words, the electrode array has a plurality of electrodes, and one of these is designed as a reference electrode. A reference signal is then measured away from any of the user's auricular muscles, by means of the reference electrode. By means of the reference signal, the sensor signal is then processed, for example freed from background noise or normalized, before it is fed to the classifier and in particular also to the feature extractor for feature analysis. It is particularly suitable to arrange the reference electrode on the mastoid, i.e. on the rough portion of the temporal bone. This ensures a sufficient reference. In addition, the reference electrode may be worn in that location largely unnoticed. In general, the reference electrode may also be suitably attached in the vicinity of the ear and operated in that position, but not directly on one of the auricular muscles.

A combination of the above embodiments is particularly advantageous wherein the electrode array has exactly one electrode and one reference electrode, i.e. a total of only two electrodes, which are both integrated into the housing of the hearing device and thus are respectively arranged close to the user's ear.

The electrodes of the electrode array, and possibly also the reference electrode, are preferably each formed as outer electrodes, i.e. as electrodes arranged outside the user's head. Alternatively, an embodiment of one or more of the electrodes as an implant is also suitable. In a suitable variant, a respective electrode is integrated into a housing of the hearing device as described above. However, an embodiment as a separate electrode, which is then connected via a signal line or wirelessly, to transmit the signals for signal processing, is also suitable.

Expediently, the electrode array for measurement is also attached to the auricular muscle and in particular to that specific muscle, so for example on the outside of the scalp, and it then measures directly on the auricular muscle, which lies under the scalp. Alternatively or in combination to the above, however, the electrode array is arranged inside the ear canal, thus still outside the head and not designed as an implant, but inserted into the ear canal. This is based on the idea that even in this location, the response behavior of the auricular muscle is measurable. Such an embodiment is particularly suitable for in-ear hearing devices, i.e. hearing devices that are worn wholly or partly in the ear canal.

The hearing device has a control unit designed to carry out a method as described above. Preferably, the classifier and the feature extractor are part of the control unit. Expediently, the learning machine is part of the control unit. In contrast, in one variant, the classifier, the feature extractor or the learning machine or a combination thereof are accommodated on an external device, for example a smartphone, which is connected to the hearing device for signal transmission. The external device then serves to relieve the hearing device of this burden, because the hearing device has limited computing power.

Preferably, the electrode array is a part of the hearing device; alternatively, the electrode array is configured as an external sensor and is coupled to the hearing device, for example by means of a cable or a wireless connection.

The hearing device is preferably a BTE device, which is worn behind the ear. This includes so-called RIC devices in which the receiver is inserted into the ear canal but the rest of the hearing device is worn outside it. However, other types such as ITE (in the ear) or CIC (completely in the ear canal) are also suitable in principle.

However, the invention is not limited to a hearing device for the care of a hearing-impaired person. In a likewise suitable embodiment, the hearing device is a headphone or a similar device for sound output. It is essential that the hearing device has a receiver for sound output.

Other features which are considered as characteristic for the invention are set forth in the appended claims.

Although the invention is illustrated and described herein as embodied in a method for operating a hearing device and a hearing device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
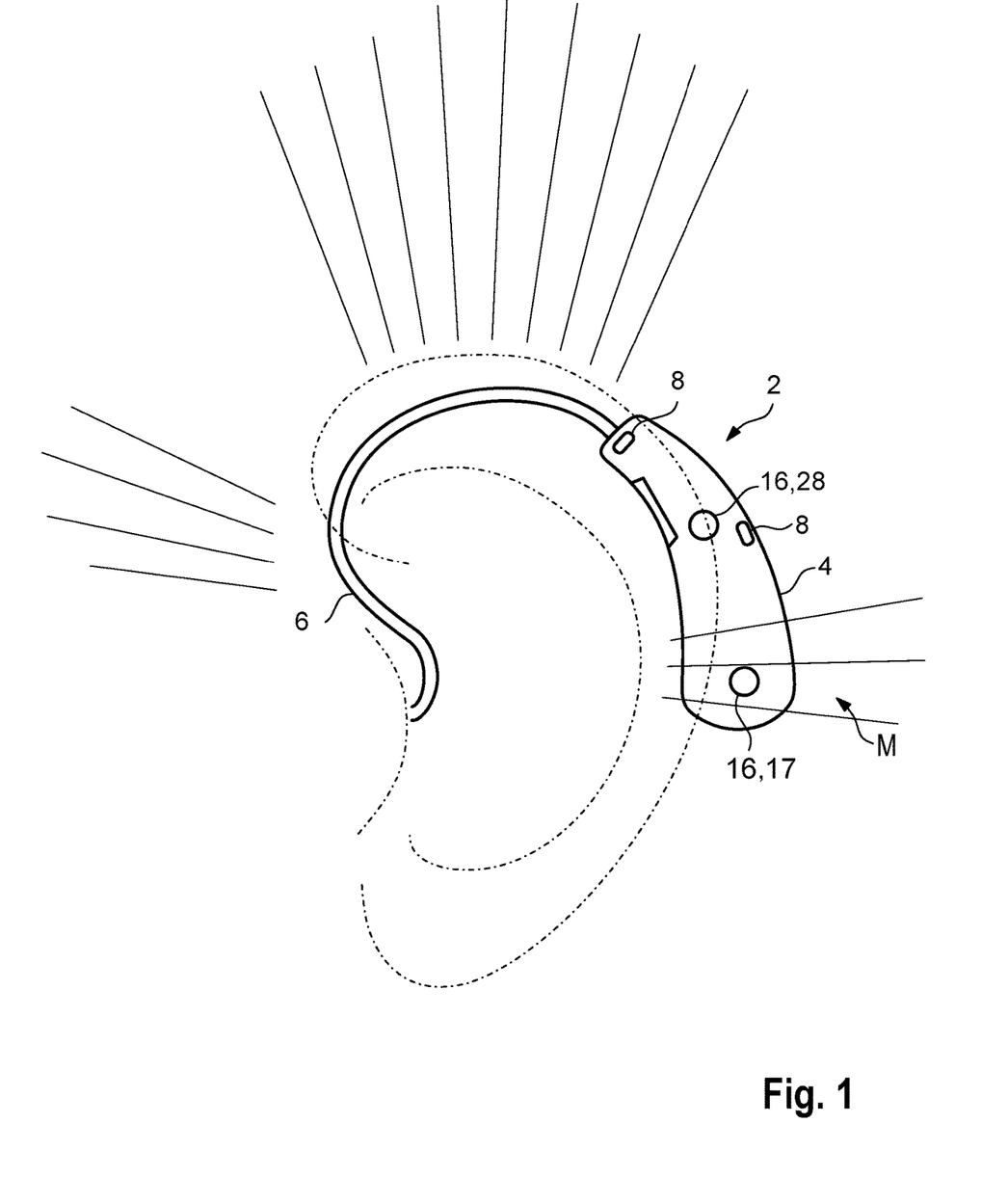
FIG. 1 is an illustration of an ear of a user and a hearing device.

Referring now to the figures of the drawings in detail and first, particularly to FIG. 1 thereof, there is shown a hearing device 2, which is worn behind an ear 0 of a user (not otherwise shown). The hearing device 2 is shown in more detail in FIG. 2. The hearing device 2 here is a BTE hearing device, with a housing 4 worn behind the ear 0, from which a sound tube 6 extends into the ear canal. The hearing device 2 also has a number of microphones 8 that record sound signals from the user's environment. These sound signals are then modified, and in particular amplified, by a control unit 10, and are then output via a receiver 12. From the receiver 12, the modified sound signals then pass through the sound tube 6 into the ear 0. For the secure holding of the sound tube 6, an earpiece 14, which is inserted into the ear canal, is attached to the end of the tube.

The hearing device 2 is operated by a method in which electromyography (EMG for short) is carried out, muscle activity of an auricular muscle M of the user being measured by means of an electrode array 16. In the present case, the electrode array 16 has a single electrode 17 and a reference electrode 28, i.e. two electrodes in total. Here, the auricular muscle M is the posterior auricular muscle, that is, the musculus auricularis posterior. Also drawn, but not explicitly indicated, are the other two extrinsic auricular muscles, namely the anterior and superior auricular muscles. Here, the electrode array 16 is a part of the housing 4 and positioned thereon in such a way that the electrode array 16 abuts the posterior auricular muscle M and thus may measure the muscular activity thereof. The muscle activity of the auricular muscle M is continuously measured so as to obtain the activity profile of the auricular muscle M. The activity profile is relatively complex, i.e. the auricular muscle M does not carry out merely individual and incoherent movements. Rather, user intention is coded in the activity profile, so that complex patterns are contained in the muscle activity over a longer measurement period of e.g. one second. These patterns are decoded in the course of the method in order to adjust the hearing device 2 optimally, i.e. to set a suitable operating mode for the current situation.

Figure 3:
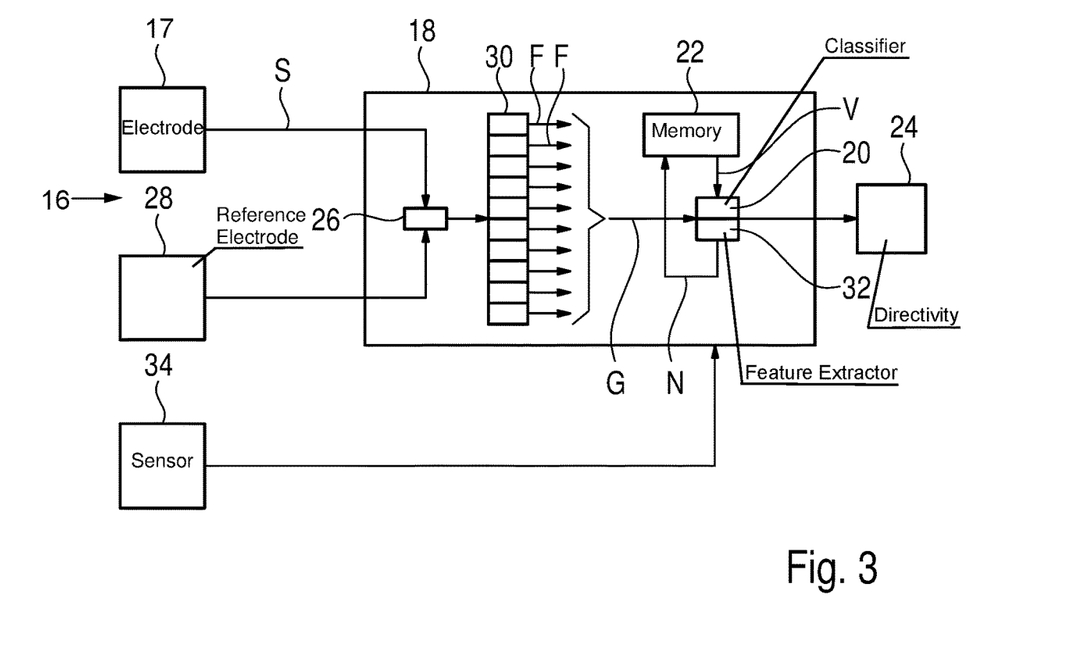
FIG. 3 is a block diagram of signal processing performed by the hearing device of FIG. 1.

The electrode array 16 generates a sensor signal S, which is supplied to a signal processor 18, which is shown in more detail in FIG. 3. The signal processor 18 is a part of the control unit 10. The signal processor 18 has a classifier 20, by means of which the sensor signal S is classified. In this case, the muscle activity is decoded and determines the underlying user's intention by examining whether the sensor signal S has a previously known feature vector V. For this purpose, a number of previously known feature vectors V are stored in a memory 22 of the signal processor 18, and these are now searched for in the sensor signal S. Each previously known feature vector V is assigned an operating mode of the hearing device 2, which is set when the sensor signal S has the previously known feature vector V. In the present case, a directional characteristic 24 is set, i.e. the hearing device 2 is designed for directional hearing and has a directional beam, with an angle and a width that are selected and adjusted based on the muscle activity and the intention coded therein, which in the present case is a hearing intention.

The process is illustrated in FIG. 3. The sensor signal S of the electrode array 16 is fed to the signal processor 18 and first prefiltered there by means of a prefilter 26. For this purpose, a sensor signal of a reference electrode 28 is used, which is a part of the electrode array 16 and is also a part of the housing 6, but is positioned away from the auricular muscles and thus provides a reference signal. In addition, noise artifacts are eliminated in the prefilter 26. The processed sensor signal S is then fed to a filter bank 30, by means of which the sensor signal S is decomposed into individual features F. The filter bank 30 has ten frequency bands. In FIG. 3, a feature F results for each frequency band. A respective feature F is, for example, the energy in the relevant frequency band, measured over the measurement period, or the entropy of the frequency band. In one variant, several features F are generated per frequency band, for example, both entropy and energy. The features F form a feature vector G, which is a feature vector G of the sensor signal S and is compared in the classifier 20 with the previously known feature vectors V. The directivity 24 is then set based on the result. This exploits the knowledge that the muscle activity, in evolutionary terms, is intended to effect an alignment of the ears O, inasmuch as an intention to hear in a particular direction is coded in the muscle activity of the auricular muscles M. An alignment of the ears O does not actually take place, but nonetheless, the control signals to the auricular muscles M are present and have a corresponding signature, which yields a corresponding activity profile and is usually user-specific. By recognizing this signature, i.e. the associated feature vector G, the intention of directional hearing is then recognized, and in this case what is recognized is not merely the fact that directional hearing is desired, but also the intended hearing direction.

In addition to the decoding of the user's intention based on the previously known feature vectors V, in this case there is also a receiving, i.e. recording, of new feature vectors N in order to recognize new and previously unknown intentions in the future. The method is therefore also a learning process, in which the hearing device 2 learns new feature vectors N and then stores them as previously known feature vectors V. For this purpose, the sensor signal S is subjected to feature extraction by means of a feature extractor 32 in which a new and in particular individual, i.e. user-specific, feature vector N is generated, which is stored in the memory 22 as an additional previously known feature vector V.

In the present case, the feature extractor 32 and the classifier 18 are integrated together in the signal processor 18, and feature extraction and classification are treated as a single optimization problem. As clearly shown in FIG. 3, the classifier 20 and the feature extractor 32 share a single feature recognition which identifies a number of features F and thus a feature vector G in the sensor signal S. The features G only need to be extracted once from the sensor signal S by means of the filter bank 30 and compared with the previously known feature vectors V, in order to then generate new feature vectors N while also recognizing the previously known feature vectors V. Because the classifier 20 and feature extractor 32 use the same filter bank 30 for feature recognition, they are both optimally matched to one another.

In the exemplary embodiment shown, new feature vectors N are learned automatically by means of a machine learning process. The analysis of the muscle activity is particularly suitable for a machine learning process, because the muscle activity is highly individual and thus may only be generalized to a limited extent. By learning new feature vectors N, a user-specific set of previously known feature vectors V is then generated through the machine learning process.

For learning new feature vectors N, a supervised machine learning process is carried out. In this case, in a training procedure, a specific situation is set up as the current situation, thereby producing a corresponding user's intention, which is then characterized by a feature vector G and linked to the operating mode. To this end, the feature extractor 32 independently searches for a number of unknown features F in the sensor signal S. The unknown features S are then combined to form the new feature vector N and this new vector is assigned to the specific operating mode. The new feature vector N is then a learned feature vector and from then on is available in the memory 22 as a previously known feature vector V.

The memory 22 is presently arranged due to the use of an SVM. When using a different machine learning concept, however, the memory 22 may be omitted under certain circumstances. Thus, in a variant not shown, a neural network is used instead of an SVM, which does not have to resort to stored feature vectors V, because these are already provided in the implementation of the neural network as a result of its structure.

It is essential to the machine learning process that the features F are not initially predetermined, but are determined independently by the feature extractor 32. For this purpose, it examines the sensor signal S according to patterns or regularities and in particular according to features F, which in combination do not correspond to any previously known feature vector V; or a search is made explicitly for features F that are similar to a previously known feature vector V in order to refine or adapt the representation thereof.

FIG. 3 further shows an additional sensor 34 which is additionally used in the context of a hybrid analysis in order to support the classification of the sensor signal S, or to support the learning process for learning new feature vectors N. The additional sensor 34 provides additional information about the environment. The additional sensor 34 is, for example, one of the microphones 8, each of which generates a microphone signal that is subjected to audio analysis in order to classify the current situation and select an appropriate operating mode. After the muscle activity and a corresponding feature vector N have been learned for this situation, future recognition is correspondingly faster and easier, without needing to resort to an expensive audio analysis. Alternatively or additionally, an EEG measurement is performed, and in that case the additional sensor 34 is a number of EEG electrodes. An acceleration sensor is also suitable as an additional sensor 34.

Figure 2:
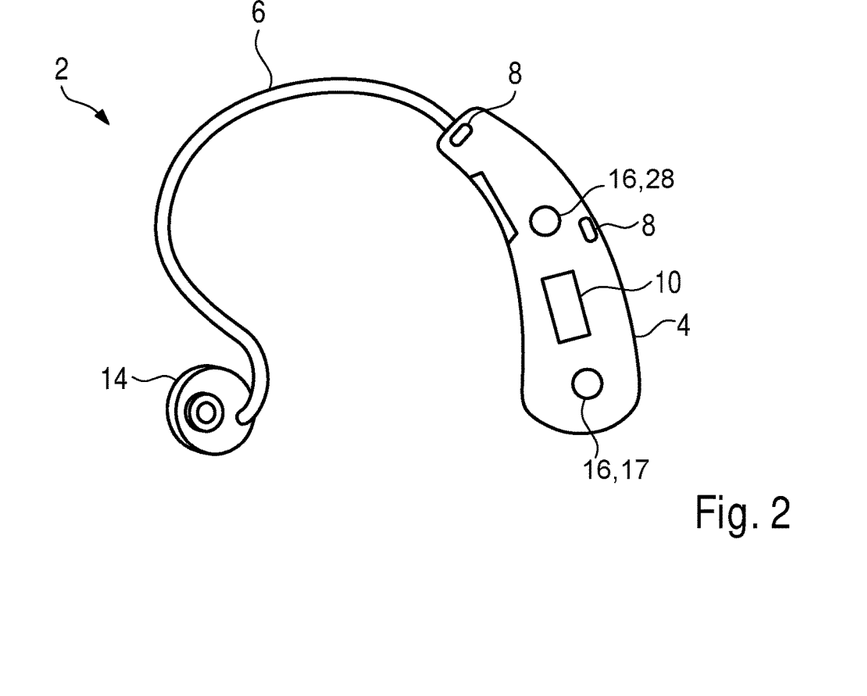
FIG. 2 is an illustration of the hearing device of FIG. 1.

In FIGS. 1 to 3, only one individual device of a hearing device 2 is shown. In one variant, however, the hearing device 2 has two corresponding individual devices, for example two individual devices each as shown in FIG. 2, which are then worn on different sides of the user's head in a manner corresponding to FIG. 1. Such a hearing device 2 is then referred to as a binaural hearing device 2. In this embodiment, therefore, two sensor signals S are available and thus more information overall, i.e. more features F, are available for classifying the user's intention and for improving the selection of a suitable operating mode.

Figure 4:
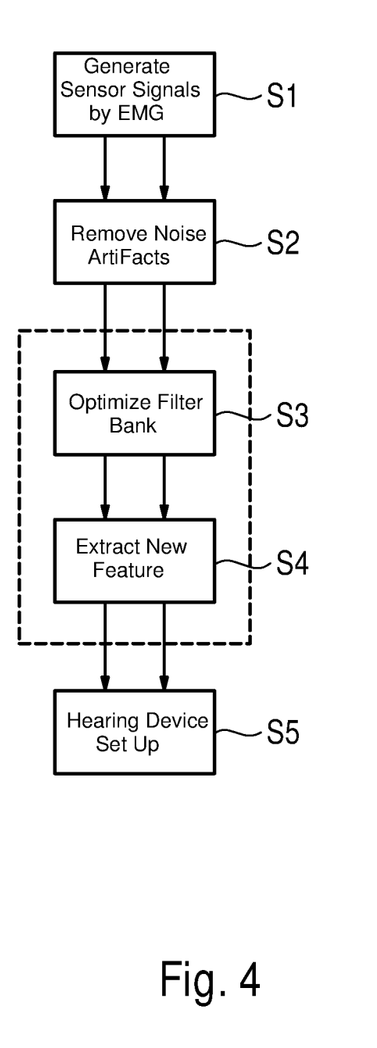
FIG. 4 is a flow chart of a machine learning process for the hearing device of FIG. 1.
Figure 5:
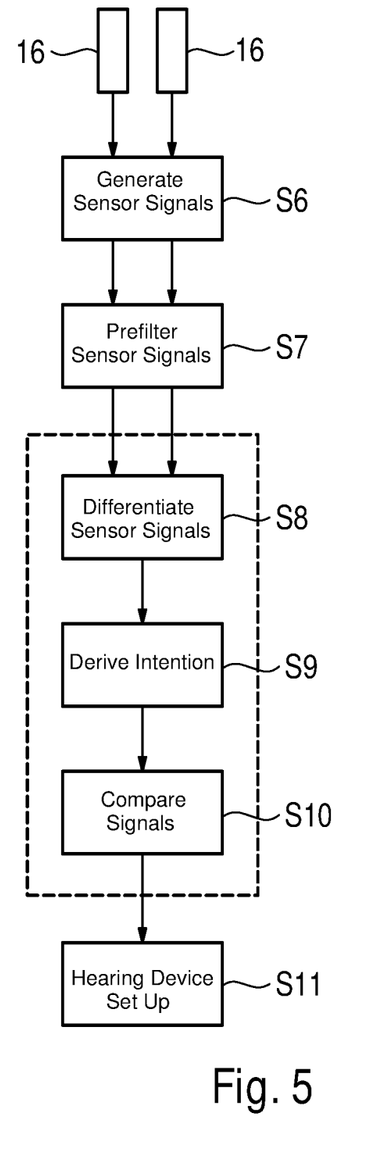
FIG. 5 is a flow chart of a method for adjusting the hearing device of FIG. 1.

An exemplary operation for such a binaural hearing device 2 is shown in FIGS. 4 and 5. In this case, a directivity 24 of the hearing device 2 is set by the sensor signals S, upon evaluating the electrode arrays 16 of the two individual devices. FIG. 4 shows the learning of new feature vectors N and the adaptation of the filter bank 30 for the optimized recognition of features F in the respective sensor signal S. Finally, FIG. 5 shows the adaptation of the directivity 24 through separate evaluation of the two sensor signals S.

In FIG. 4, in the first step S1, the sensor signals S are generated separately by means of EMG. In step S2, noise artifacts are removed by means of the prefilter 26. Steps S3 and S4 relate to the adaptation and setting of the feature recognition and the filter bank 30, in the course of the machine learning process. In step S3, the parameterized filter bank 30 is optimized, in particular so that the two sensor signals S may be distinguished in order to be able to assign respective features F to the right or the left side. In step S4, a new feature vector N is extracted to be stored as a previously known feature vector V for the classifier 20. In step S5, the hearing device is then optimally set up, i.e. personalized, for the respective user.

FIG. 5 shows how the previously known feature vectors V are used for classification in directional hearing. The evaluation of the muscle activities of the auricular muscles M on the two sides is first carried out separately by independently classifying the sensor signals S, and then the hearing device 2 is adjusted only if the results match. In this way, a comparative decision-making process takes place. In step S6, the sensor signals S are generated by means of the electrode arrays 16. In step S7, the sensor signals S are prefiltered as in step S2 in FIG. 4. The previously optimized filter bank 30 then differentiates the two sensor signals S in step S8 and independently determines their characteristics F. Two feature vectors G are then generated, from which a specific intention is derived through classification in step S9. These signals are compared in step S10. If the results for both sides agree, the hearing device 2 is set accordingly in step S11.

The following is a summary list of reference numerals and the corresponding structure used in the above description of the invention:
2 Hearing device
4 Housing
6 Sound tube
8 Microphone
10 Control unit
12 Receiver
14 Earpiece
16 Electrode array
17 Electrode
18 Signal processing
20 Classifier
22 Memory
24 Directivity
26 Prefilter
28 Reference electrode
30 Filter bank
32 Feature extractor
34 Additional sensor
F Feature
G Feature vector
M Auricular muscle
N New feature vector
O Ear
S Sensor signal
V Previously known feature vector

The invention claimed is:

1. A method for operating a hearing device of a user, which comprises the steps of:
carrying out an electromyography step in which muscle activity of an auricular muscle of the user is measured using an electrode array;
continuously measuring the muscle activity to detect a complex activity profile of the auricular muscle in which an underlying intention of the user is coded;
generating, via the electrode array, a sensor signal that is classified by means of a classifier in which the muscle activity is decoded and the underlying intention is determined by examining whether the sensor signal has a previously known feature vector; and
assigning the previously known feature vector to an operating mode of the hearing device that is set if the sensor signal has the previously known feature vector.

2. The method according to claim 1, which further comprises measuring the muscle activity over a measurement period of at least 100 ms and that the previously known feature vector is searched for in the sensor signal over an entire measurement period.

3. The method according to claim 1, which further comprises:
configuring the hearing device for directional hearing; and
adjusting a directivity of the hearing device on a basis of the muscle activity, and a sound source in a specific direction is emphasized.

4. The method according to claim 3, wherein the hearing device is a binaural hearing device and has two individual devices to be worn on different sides of a head of the user, and the sensor signal is generated on each of the different sides by means of the electrode array and the muscular activity of the auricular muscle is measured.

5. The method according to claim 4, wherein the muscle activities on both of the different sides are first evaluated separately by classifying sensor signals independently of one another, and then, if results agree, the hearing device is set.

6. The method according to claim 4, wherein muscle activities on both of the different sides are first evaluated separately by classifying the sensor signals independently of one another, and if results differ, the individual devices are synchronized by adjusting one of the individual devices against its own result and with reference to a result of the other of the individual devices.

7. The method according to claim 4, wherein the underlying intention is a desired hearing direction, which is determined by examining which of the two sensor signals has a higher degree of organization or a higher energy, and the directivity is adjusted toward the hearing direction.

8. The method according to claim 1, wherein an own-voice situation, in which the user is speaking, is recognized based on the muscle activity, and the operating mode is an own-voice reduction in which a natural voice component is reduced in an output signal of the hearing device.

9. The method according to claim 1, wherein a facial expression of the user is recognized on a basis of the muscle activity, and is used as a control command for setting a specific operating mode that is assigned to the control command.

10. The method according to claim 1, wherein faulty positioning of the hearing device is recognized based on the muscle activity.

11. The method according to claim 1, which further comprises setting an amplification scheme, a compression scheme or a noise suppression of the hearing device, based on the muscle activity.

12. The method according to claim 1, wherein the previously known feature vector is stored in an external database.

13. The method according to claim 1, which further comprises subjecting the sensor signal to feature extraction by means of a feature extractor, in which a new feature vector is generated which is stored as an additional previously known feature vector.

14. The method according to claim 13 which further comprises generating the new feature vector in a supervised machine learning process, wherein:
 a particular operating mode is assigned to a particular situation;
 the particular situation is generated as a current situation;
 the feature extractor independently searches for a number of unknown features in the sensor signal;
 the unknown features are combined to form the new feature vector; and
 the new feature vector is assigned to the particular operating mode.

15. The method according to claim 14, which further comprises carrying out the supervised machine learning process during normal operation of the hearing device, with the feature extractor continuously examining whether the new feature vector is contained in the sensor signal.

16. The method according to claim 14, wherein:
 by means of an additional sensor it is recognized whether the current situation is a previously known situation already associated with a previously known operating mode; and
 if the current situation corresponds to the previously known situation, the new feature vector is assigned to the previously known operating mode.

17. The method according to claim 13, which further comprises integrating the feature extractor and the classifier together into a signal processor, and the feature extraction and classification are treated as a single optimization problem.

18. The method according to claim 14, which further comprises integrating the previously known feature vector into a neural network, by means of the neural network it is examined whether the sensor signal has the previously known feature vector, by determining a feature vector of the sensor signal and using it as an input signal for the neural network.

19. The method according to claim 18, which further comprises recognizing by means of an additional sensor whether the current situation is a previously known situation already associated with a previously known operating mode, and if an integrated feature vector coincides with the feature vector of the sensor signal, the feature vector is integrated into the neural network which is assigned to the previously known operating mode.

20. The method according to claim 1, which further comprises dividing the sensor signal into a plurality of frequency bands by a filter bank, with each frequency band forming a number of features.

21. The method according to claim 20, wherein the filter bank is a paraunitary and parameterized filter bank.

22. The method according to claim 20, wherein the filter bank has a lower limit frequency of 4 Hz and an upper limit frequency of 1 kHz, so that the muscle activity is examined in a frequency range from 4 Hz to 1 kHz.

23. The method according to claim 1, wherein the electrode array has at most five electrodes.

24. The method according to claim 1, wherein the electrode array has a plurality of electrodes, one of the electrodes is a reference electrode, by means of which a reference signal is measured away from the auricular muscle of the user, and in that the sensor signal is prepared by means of the reference signal before the sensor signal is fed to the classifier.

25. A hearing device, comprising:
 a control unit for operating the hearing device, said control unit programmed to:
  carry out an electromyography step in which muscle activity of an auricular muscle of a user is measured using an electrode array;
  continuously measure the muscle activity to detect a complex activity profile of the auricular muscle in which an underlying intention of the user is coded;
  generate, via the electrode array, a sensor signal that is classified by means of a classifier in which the muscle activity is decoded and the underlying intention is determined by examining whether the sensor signal has a previously known feature vector; and
  assign the previously known feature vector to an operating mode of the hearing device that is set if the sensor signal has the previously known feature vector.

* * * * *